(12) United States Patent
Lee et al.

(10) Patent No.: US 8,481,215 B2
(45) Date of Patent: Jul. 9, 2013

(54) ELECTROLYTE HAVING EUTECTIC MIXTURE AND ELECTROCHEMICAL DEVICE CONTAINING THE SAME

(75) Inventors: Byoung-Bae Lee, Chungcheongnam-do (KR); Jae-Seung Oh, Seoul (KR); Ji-Won Park, Daejeon (KR); Dong-Su Kim, Daejeon (KR); Hyo-Jin Lee, Daejeon (KP); Yeon-Suk Hong, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 13/055,520

(22) PCT Filed: Jul. 24, 2009

(86) PCT No.: PCT/KR2009/004146
§ 371 (c)(1),
(2), (4) Date: Jan. 24, 2011

(87) PCT Pub. No.: WO2010/011110
PCT Pub. Date: Jan. 28, 2010

(65) Prior Publication Data
US 2011/0117422 A1    May 19, 2011

(30) Foreign Application Priority Data
Jul. 25, 2008  (KR) .................. 10-2008-0072804

(51) Int. Cl.
*H01M 6/14*    (2006.01)

(52) U.S. Cl.
USPC .......................................... 429/303; 429/188

(58) Field of Classification Search
None
See application file for complete search history.

(56) References Cited

U.S. PATENT DOCUMENTS
2007/0099090 A1 *  5/2007  Oh et al. .................. 429/339

FOREIGN PATENT DOCUMENTS

| | | | |
|---|---|---|---|
| JP | 2000-348760 A | | 12/2000 |
| JP | 2000348760 A | * | 12/2000 |
| KR | 100751203 B1 | | 8/2007 |
| KR | 20070085575 A | | 8/2007 |
| WO | 2006059085 A1 | | 6/2006 |
| WO | 2007021151 A1 | | 2/2007 |

OTHER PUBLICATIONS

International Search Report, PCT/KR2009/004146, dated Feb. 19, 2010.

* cited by examiner

*Primary Examiner* — Ula C Ruddock
*Assistant Examiner* — Scott J Chmielecki
(74) *Attorney, Agent, or Firm* — Lerner, David, Littenberg, Krumholz & Mentlik, LLP

(57) ABSTRACT

An electrolyte includes (a) a eutectic mixture of an alkoxy alkyl group-containing amide compound and an ionizable lithium salt; and (b) a carbonate-based compound. The electrolyte has excellent thermal and chemical stability and exhibits a low lowest limit of electrochemical window. Also, the electrolyte shows low viscosity and high ion conductivity, so it may be usefully applied as an electrolyte of electrochemical devices using various anode materials.

20 Claims, 2 Drawing Sheets

ELECTROLYTE HAVING EUTECTIC MIXTURE AND ELECTROCHEMICAL DEVICE CONTAINING THE SAME

CROSS REFERENCE TO RELATED APPLICATIONS

The present application is a national phase entry under 35 U.S.C. §371 of International Application No. PCT/KR2009/004146, filed Jul. 24, 2009, published in Korean, which claims the benefit of Korean Patent Application No. 10-2008-0072804 dated Jul. 25, 2008. The disclosures of said applications are incorporated by reference herein.

TECHNICAL FIELD

The present invention relates to an electrolyte having a eutectic mixture, and an electrochemical device containing the same.

BACKGROUND ART

Various kinds of electrolytes are recently used for many electrochemical devices such as lithium secondary batteries, electrolytic condensers, electric double-layer capacitors, electrochromic display devices, and dye-sensitized solar cells that are currently studied in various ways for further usage, and the importance on electrolytes is increased day by day.

In particular, lithium secondary batteries are most highlighted as a battery with high energy density and long life cycle. Generally, a lithium secondary battery includes an anode made of carbon material or lithium metal alloy, a cathode made of lithium metal oxide, and an electrolyte made by dissolving lithium salt in an organic solvent. Structural stability and capacity of lithium metal oxides are determined according to intercalation and disintercalation reactions of lithium ions. The capacity of lithium metal oxides is increased as a charge potential is raised, but the lithium metal oxides become structurally unstable accordingly. Such unstable structure of the electrode results in generation of oxygen, which may cause overheating in a battery or reaction with the electrolyte, possibly resulting explosion of the battery.

In recent, organic solvents most frequently used for electrolyte of a lithium secondary battery include ethylene carbonate, propylene carbonate, dimethoxy ethane, γ-butyrolactone (GBL), N,N-dimethyl formamide, tetrahydrofurane and acetonitrile. These organic solvents generally have high volatility and high ignitability, so a lithium secondary battery adopting such organic solvents may exhibit a problem in its stability, particularly high temperature stability.

In order to solve this problem, there has been proposed a method of using an imidazolium-based or ammonium-based ionic liquid as an electrolyte of a lithium secondary battery. However, such an ionic liquid may be reduced at a higher voltage than lithium ions in an anode, or imidazolium or ammonium cations may be inserted into the anode together with lithium ion, which rather deteriorates the battery performance.

Meanwhile, Korean Patent Registration No. 10-751203 and Korean Laid-open Patent Publication No. 10-2007-85575 disclose eutectic mixtures of lithium salt and amide compound such as acetamide, urea, methylurea, caprolactam, valerolactam, trifluoroacetamide, carbamate and formamide, expressed as predetermined chemistry figures, as an electrolyte. Such eutectic mixtures exhibit high thermal and chemical stabilities as well as relatively wide electrochemical window, so they solve the problems such as evaporation or ignition of electrolyte caused by the usage of the existing organic solvents.

Accordingly, the development of various eutectic mixtures as electrolyte is accelerated. In particular, there is an increased demand on eutectic mixture electrolytes having better high temperature stability and a smaller lowest limit of an electrochemical window for the use in electrochemical devices requiring various electrochemical characteristics.

DISCLOSURE

[Technical Problem]

Therefore, it is an object of the present invention to provide an electrolyte exhibiting high thermal and chemical stabilities, and an electrochemical device containing the same.

Another object of the present invention is to provide an electrolyte having an eutectic mixture, which ensures better high temperature stability, gives a smaller lowest limit of an electrochemical window, and exhibits sufficiently low viscosity and high ion conductivity, and an electrochemical device containing the same.

[Technical Solution]

In one aspect of the present invention, there is provided an electrolyte, which includes (a) a eutectic mixture of an alkoxy alkyl group-containing amide compound expressed by the following chemistry figures 1 or 2 and an ionizable lithium salt; and (b) a carbonate-based compound,

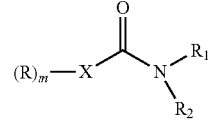

Chemistry Figure 1 where R, $R_1$ and $R_2$ are hydrogen, halogen or any one selected from the group consisting of alkyl group, alkylamine group, alkenyl group and aryl group having 1 to 20 carbons, independently, and at least one of $R_1$ and $R_2$ is an alkoxy alkyl group expressed by $CH_3-(CH_2)p-O(CH_2)q$, where p is an integer of 0 to 8 and q is an integer of 1 to 8, and where X is any one selected from the group consisting of silicon, oxygen, nitrogen, phosphorus, sulfur and hydrogen, wherein i) m is 0 (zero) when X is hydrogen, ii) m is 1 when X is oxygen or sulfur, iii) m is 2 when X is nitrogen or phosphorus, and iv) m is 3 when X is silicon;

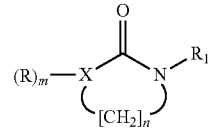

Chemistry Figure 2 where R is hydrogen, or any one selected from the group consisting of alkyl group, alkylamine group, alkenyl group, aryl group and allyl group having 1 to 20 carbons, and $R_1$ is an alkoxy alkyl group expressed by $CH_3-(CH_2)p-O(CH_2)q$, where p is an integer of 0 to 8 and q is an integer of 1 to 8, where X is any one selected from the group consisting of silicon, oxygen, nitrogen, phosphorus and sulfur, wherein i) m is 0 (zero) when X is oxygen or sulfur, ii) m is 1 when X is nitrogen or phosphorus, and iii) m is 2 when X is silicon, and where n is an integer of 1 to 10.

In the electrolyte according to the present invention, the alkoxy alkyl group-containing amide compound may be any one selected from the group consisting of N-methoxyethyl methylcarbamate, N-methoxyethyl-N-methyl methylcarbamate, N-methoxymethyl-N-methyl methylcarbamate, N,N-dimethyl methoxyethyl carbamate, N-methyl-methoxymethyl methoxyethyl carbamate, N-methyl-N-methoxyethyl methoxyethyl carbamate, N-methyl-N-methoxyethyl methoxymethyl carbamate, N-methoxyethyl caprolactam, N-methoxyethyl oxazolidinone, N-methoxyethyl-N-methyl phenyl thiocarbamate, and N-methoxyethyl-N-methyl piperidine carbamate.

In addition, in the electrolyte according to the present invention, an anion of the lithium salt may be any one selected from the group consisting of $F^{31}$, $Cl^-$, $I^{31}$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$ and $(CF_3CF_2SO_2)_2N^-$.

In the electrolyte according to the present invention, the eutectic mixture including the alkoxy alkyl group-containing amide compound expressed by the chemistry FIG. 1 and the ionizable lithium salt preferably has a reduction potential window of 0.4 to 0.55V, and the eutectic mixture including the alkoxy alkyl group-containing amide compound expressed by the chemistry figure 2 and the ionizable lithium salt preferably has a reduction potential window of 0.7 to 0.9V.

In the electrolyte according to the present invention, the carbonate-based compound may use any carbonate compound commonly used as an organic solvent of an electrolyte, and for example linear carbonate and cyclic carbonate may be used solely or in combination.

In the electrolyte according to the present invention, the electrolyte preferably has a viscosity of 4 to 30 cP.

In addition, the electrolyte of the present invention may be a liquid electrolyte, or a solid or gel-type polymer electrolyte made of polymer itself, and the polymer electrolyte may be a gel-type polymer electrolyte formed by polymerizing a precursor solution containing the eutectic compound and a monomer that may form a polymer by polymerization reaction, or the polymer electrolyte may be obtained by impregnating the eutectic polymer in a polymer.

The above electrolyte of the present invention may be usefully applied to an electrochemical device such as a lithium secondary battery.

[Advantageous Effect]

The electrolyte according to the present invention gives the following effects.

First, since the new eutectic mixture included in the electrolyte of the present invention exhibits inherent characteristics of the eutectic mixture such as excellent thermal stability and excellent chemical stability, the conventional problems of electrolyte solution such as evaporation, ignition and side reaction may be greatly solved.

Second, the electrolyte of the present invention may give a lowest limit of the electrochemical window, or a low reduction potential window, so the electrolyte may be usefully applied to electrochemical devices that require various electrochemical characteristics.

Third, the electrolyte of the present invention exhibits sufficiently low viscosity and ion conductivity, so an electrochemical device containing the electrolyte may exhibit good charging/discharging performance.

BEST MODE

Hereinafter, preferred embodiments of the present invention will be described in detail. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation.

Figure 1:
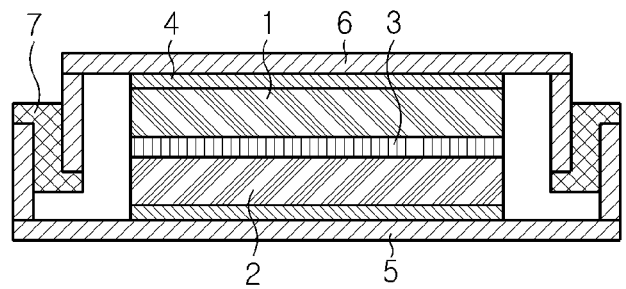
FIG. 1 is a schematic view showing a coin-type secondary battery.
Figure 2:
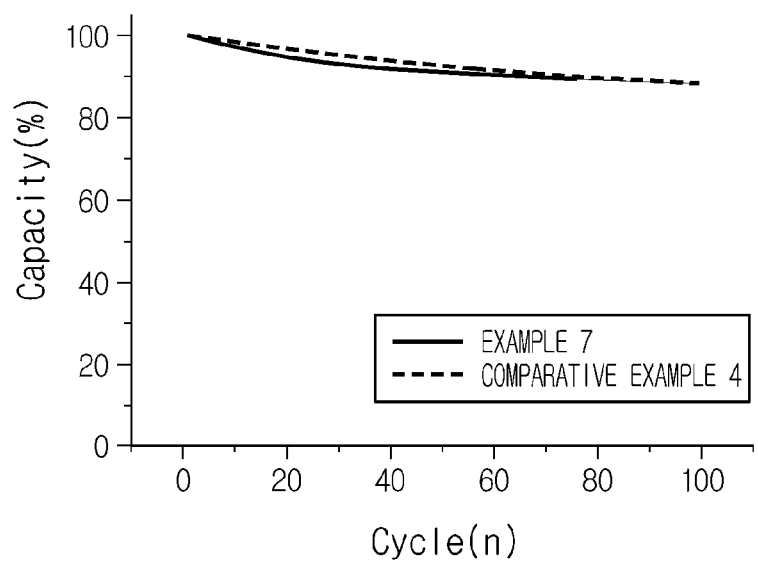
FIG. 2 is a graph showing charging/discharging efficiency of secondary batteries according to an example 7 and a comparative example 4.

An electrolyte according to the present invention includes (a) a eutectic mixture of an alkoxy alkyl group-containing amide compound expressed by the following chemistry FIG. 1 or 2 and an ionizable lithium salt; and (b) a carbonate-based compound.

[Chemistry Figure 1]

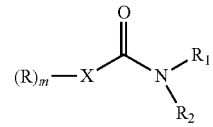

where R, $R_1$ and $R_2$ are hydrogen, halogen or any one selected from the group consisting of alkyl group, alkylamine group, alkenyl group and aryl group having 1 to 20 carbons, independently, and at least one of $R_1$ and $R_2$ is an alkoxy alkyl group expressed by $CH_3-(CH_2)p-O(CH_2)q$, where p is an integer of 0 to 8 and q is an integer of 1 to 8; and where X is any one selected from the group consisting of silicon, oxygen, nitrogen, phosphorus, sulfur and hydrogen, wherein i) m is 0 (zero) when X is hydrogen, ii) m is 1 when X is oxygen or sulfur, iii) m is 2 when X is nitrogen or phosphorus, and iv) m is 3 when X is silicon.

Chemistry Figure 2

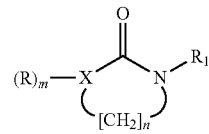

where R is hydrogen, or any one selected from the group consisting of alkyl group, alkylamine group, alkenyl group, aryl group and allyl group having 1 to 20 carbons, and $R_1$ is an alkoxy alkyl group expressed by $CH_3-(CH_2)p-O(CH_2)q$, where p is an integer of 0 to 8 and q is an integer of 1 to 8;

where X is any one selected from the group consisting of silicon, oxygen, nitrogen, phosphorus and sulfur, wherein i) m is 0 (zero) when X is oxygen or sulfur, ii) m is 1 when X is nitrogen or phosphorus, and iii) m is 2 when X is silicon; and where n is an integer of 1 to 10.

Electrochemical devices generate much heat in use or are frequently exposed to high temperature, so stability at high temperature is a very important factor.

The inventors formed a eutectic mixture using the alkoxy alkyl group-containing amide compound, mentioned above, together with a lithium salt. This eutectic mixture exhibits high thermal and chemical stabilities, differently from existing non-aqueous electrolyte organic solvent, and the thermal and chemical stabilities of the above eutectic mixture were superior to those of a eutectic mixture of lithium salt and amide-based compound like methyl carbamate. Also, the eutectic mixture of lithium salt and alkoxy alkyl group-containing amide compound according to the present invention may exhibit a lowest limit of an electrochemical window (or, also called a potential window) that is small. For example, the eutectic mixture of an alkoxy alkyl group-containing amide compound expressed by the following chemistry figure 1 and an ionizable lithium salt preferably has a reduction potential window of 0.4 to 0.55V, and the eutectic mixture of an alkoxy alkyl group-containing amide compound expressed by the following chemistry FIG. 2 and an ionizable lithium salt preferably has a reduction potential window of 0.7 to 0.9V.

Accordingly, the electrolyte containing the eutectic mixture of lithium salt and alkoxy alkyl group-containing amide compound contributes to improvement of high temperature stability of secondary batteries, and they may be usefully applied as electrolyte of secondary batteries having various anode materials.

In the electrolyte of the present invention, the alkoxy alkyl group-containing amide compound of the eutectic mixture may be N-methoxyethyl methylcarbamate, N-methoxyethyl-N-methyl methylcarbamate, N-methoxymethyl-N-methyl methylcarbamate, N,N-dimethyl methoxyethyl carbamate, N-methyl-methoxymethyl methoxyethyl carbamate, N-methyl-N-methoxyethyl methoxyethyl carbamate, N-methyl-N-methoxyethyl methoxymethyl carbamate, N-methoxyethyl caprolactam, N-methoxyethyl oxazolidinone, N-methoxyethyl-N-methyl phenyl thiocarbamate, N-methoxyethyl-N-methyl piperidine carbamate, or the like.

In addition, in the electrolyte of the present invention, the lithium salt that configures the eutectic mixture together with the alkoxy alkyl group-containing amide compound is an ionizable lithium salt, which may be expressed as $Li^+X^-$. This lithium salt may have an anion such as $F^-$, $Cl^-$, $Br^-$, $I^-$, $NO_3^-$, $N(CN)_2^-$, $BF_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$ and $(CF_3CF_2SO_2)_2N^-$, though not limited thereto.

The eutectic mixture included in the electrolyte of the present invention has a melt temperature that may be varied depending on R, $R_1$, $R_2$ and X of the chemistry figure 1 or 2, but preferably the eutectic mixture exists in a liquid state at a temperature of 25° C. or below, in other words at a normal temperature (25° C.).

Meanwhile, the electrolyte of the present invention includes a carbonate-based compound.

Ion conductivity is generally determined according to the degree of mobility of ions moving in an electrolyte solution, so viscosity of the electrolyte solution and ion concentration in the electrolyte solution are factors affecting on the ion conductivity. As the viscosity of the solution is lower, ions may more freely move in the solution, and the ion conductivity is increased. On the while, as the ion concentration is higher in the solution, an amount of ions serving as charge carriers is increased, and thus the ion conductivity is increased. The electrolyte of the present invention uses a carbonate-based compound in the eutectic mixture, which lowers viscosity of the electrolyte and thus improves ion conductivity. In this point of view, the electrolyte according to the present invention preferably has a viscosity of 50 cP or less, more preferably 4 to 30 cP in consideration of ion conductivity and thermal stability of the electrolyte. In the same view, the electrolyte preferably has an ion conductivity of 5 to 10 mS/cm.

In order to have the above viscosity and ion conductivity, the carbonate-based compound is preferably included in the content of 5 to 200 parts by weight, based on 100 parts by weight of the eutectic mixture.

The carbonate-based compound included in the electrolyte of the present invention may use any carbonate compound commonly used in non-aqueous electrolytes of lithium secondary batteries, and linear carbonate-based compounds and cyclic carbonate-based compounds may be used in single or in mixture. Such carbonate-based compounds may be propylene carbonate (PC), ethylene carbonate (EC), diethyl carbonate (DEC), dimethyl carbonate (DMC), dipropyl carbonate (DPC), butylene carbonate, methylpropyl carbonate, ethylpropyl carbonate, dimethyl sulfoxide, acetonitrile, dimethoxyethane, diethoxyethane, tetrahydrofuran, N-methyl-2-pyrrolidone (NMP), ethylmethyl carbonate (EMC) or γ-butyrolactone), or their mixtures. Such carbonate-based compounds may be substituted with halogen atom, as mentioned above.

The electrolyte of the present invention may be prepared in a common way well known in the art. For example, the electrolyte may be obtained by mixing the alkoxy alkyl group-containing amide compound with a lithium salt at a normal temperature, and then adding a carbonate-based compound thereto or mixing an amide group-containing compound, a carbonate-based compound and a lithium salt thereto at a normal temperature, and then applying a suitable temperature not higher than 70° C. thereto to react and purify them. At this time, in the prepared eutectic mixture contained in the electrolyte, the alkoxy alkyl group-containing amide compound and the lithium salt are preferably included at a mole ratio of 1~8:1, more preferably 2~6:1, in consideration of ion conductivity and viscosity.

Meanwhile, it would be apparent to those having ordinary skill in the art that various kinds of additives or organic solvents may be further included in the electrolyte of the present invention if they do not deteriorate the inherent effects of the present invention.

The electrolyte of the present invention may use all kinds of electrolytes regardless of their forms, for example liquid electrolyte and solid or gel-type polymer electrolyte made of polymer itself.

In case the electrolyte of the present invention is a polymer electrolyte, the electrolyte may be a gel-type polymer electrolyte formed by polymerizing a precursor solution containing a monomer and a mixture of the eutectic compound and the carbonate-based compound at the same time, or the electrolyte may be prepared as a polymer electrolyte where a mixture of the eutectic mixture and the carbonate-based compound is impregnated in a solid or gel-type polymer.

First, the gel-type polymer electrolyte prepared by polymerization of a precursor solution is explained.

The gel-type polymer electrolyte according to one aspect of the present invention may be formed by polymerizing a precursor solution to which (i) a mixture of the eutectic mixture in the above (a) section and the carbonate-based compound in the above (b) section; and (ii) a monomer are added at the same time.

The monomer may use all kinds of monomers that may form a gel polymer together with the eutectic mixture and the carbonate-based compound while polymerization reaction progresses, and it may be a vinyl monomer, but not limited thereto. The vinyl monomer allows very simple polymerization when it is mixed with a mixture of the eutectic mixture and the carbonate-based compound to form a gel polymer.

The vinyl monomer may be acrylonitrile, methylmethacrylate, methylacrylate, methacrylonitrile, methylstyrene, vinylester, vinyl chloride, vinylidene chloride, acrylamide, tetrafluoroethylene, vinylacetate, methylvinylketone, ethylene, styrene, paramethoxystyrene and paracyanostyrene, or their mixtures, but not limitedly.

The precursor solution may additionally include common polymerization initiators or photo initiators. The initiator is decomposed by heat or UV rays to form radicals, and then forms a gel polymer electrolyte by reacting with the monomer by free radical polymerization. In addition, the monomer may also be polymerized without using an initiator. Generally, the free radical polymerization goes through an initiation reaction by which temporary molecules or active sites with strong reactivity are formed, a propagation reaction by which a monomer is added to an activation chain terminal to form an active site at the end of the chain, a chain transfer reaction by which the active sites are transferred to other molecules, and a termination reaction by which the activation chain center is destroyed.

Allowable thermal polymerization initiators may be organic peroxides or hydroperoxides such as benzoyl peroxide, acetyl peroxide, dilauryl peroxide, di-tert-butyl peroxide, cumyl hydroperoxide and hydrogen peroxide; azo compounds such as 2,2-azobis(2-cyanobutane), 2,2-azobis(methylbutyronitrile), AIBN (azobis(iso-butyronitrile) and AMVN (azobisdimethyl-valeronitrile); organic metals such as alkylated silvers; and so on, but not limitedly. Also, the photo initiator that forms radicals by light such as UV rays may be chloroacetophenone, diethoxy acetophenone (DEAP), 1-phenyl-2-hydroxy-2-methyl propaneone (HMPP), 1-hydroxy cyclohexyl phenyl ketone, α-amino acetophenone, benzoin ether, benzyl dimethyl ketal, benzophenone, thioxanthone, 2-ethylanthraquinone (2-ETAQ) and so on.

In addition to the above components, the precursor solution of the gel polymer electrolyte employed in the present invention may selectively contain other additives well known in the art.

The above precursor solution is used to form a gel polymer electrolyte in a common way well known in the art. At this time, the gel polymer electrolyte is preferably prepared by means of in-situ polymerization reaction in an electrochemical device. The in-situ polymerization reaction may be conducted using heat or UV irradiation. A content ratio of the (i) component to the (ii) component may be controlled to for example 0.5~0.95:0.05~0.5. The degree of polymerization of the gel polymer may be adjusted depending on reaction factors such as polymerization time, polymerization temperature and amount of irradiated light, so the degree of polymerization is controlled such that polymer is not over-polymerized to shrink its volume without any leakage of electrolyte.

As another method for preparing a polymer electrolyte according to the present invention, it is possible to inject a mixture of the eutectic mixture and the carbonate-based compound to a previously prepared solid or gel polymer such that the electrolyte is impregnated in the polymer.

Available polymers include polymethylmethacrylate, polyvinylidene difluoride, polyvinyl chloride, polyethylene oxide and polyhydroxyethylmethacrylate, which may be used in single or in mixture, but not limitedly. This method may be simplified using the above in-situ polymerization.

As another method for preparing a polymer electrolyte according to the present invention, it is also possible to dissolve a polymer and a mixture of the eutectic mixture and the carbonate-based compound in a solvent and then eliminating the solvent to form a polymer electrolyte. At this time, the electrolyte is in a state of being contained in a polymer matrix.

Available solvents are not specially limited, but the solvent may be toluene, acetone, acetonitrile, THF and so on. Also, the solvent may be eliminated in various ways such as heating, without special limitations.

The electrolyte according to the present invention as described above may be usefully applied to electrochemical devices such as lithium secondary batteries. A lithium secondary battery to which the electrolyte of the present invention is applied has excellent thermal stability. Thus, though a pouch-type secondary battery to which the electrolyte of the present invention is applied is charged to 4.2V and then left alone at 90° C. for 4 hours, the pouch-type secondary battery may have a thickness change ratio of 10% or less.

[Mode for Invention]

Hereinafter, various preferred examples of the present invention will be described in detail for better understandings. However, the examples of the present invention may be modified in various ways, and they should not be interpreted as limiting the scope of the invention. The examples of the present invention are just for better understandings of the invention to persons having ordinary skill in the art.

Preparation of Electrolyte

EXAMPLE 1

4.1 g of N-methoxyethyl-N-methyl methylcarbamate and 2 g of $LiPF_6$ were put into a round bottom flask and slowly stirred for 2 hours under a nitrogen circumstance, and then 1.7 g of ethylmethylcarbonate was added thereto, thereby obtaining 7.8 g of a desired electrolyte.

EXAMPLE 2

3.6 g of N-methoxyethyl methylcarbamate and 2 g of $LiPF_6$ were put into a round bottom flask and slowly stirred for 2 hours under a nitrogen circumstance, and then 1.6 g of ethylmethylcarbonate was added thereto, thereby obtaining 7.2 g of a desired electrolyte.

EXAMPLE 3

5.2 g of N-methoxyethyl-N-methyl methoxyethyl carbamate and 2 g of $LiPF_6$ were put into a round bottom flask and slowly stirred for 2 hours under a nitrogen circumstance, and then 2.3 g of ethylmethylcarbonate was added thereto, thereby obtaining 9.5 g of a desired electrolyte.

EXAMPLE 4

4.0 g of N-methoxyethyl oxazolidinone and 2 g of $LiPF_6$ were put into a round bottom flask and slowly stirred for 2 hours under a nitrogen circumstance, and then 1.7 g of ethylmethylcarbonate was added thereto, thereby obtaining 7.7 g of a desired electrolyte.

EXAMPLE 5

3.8 g of N-methoxyethyl-N-methyl phenyl thiocarbamate and 2 g of $LiPF_6$ were put into a round bottom flask and slowly stirred for 2 hours under a nitrogen circumstance, and then 1.7 g of ethylmethylcarbonate was added thereto, thereby obtaining 7.4 g of a desired electrolyte.

EXAMPLE 6

3.6 g of N-methoxyethyl-N-methyl piperidine carbamate and 2 g of $LiPF_6$ were put into a round bottom flask and slowly stirred for 2 hours under a nitrogen circumstance, and then 1.7 g of ethylmethylcarbonate was added thereto, thereby obtaining 7.1 g of a desired electrolyte.

COMPARATIVE EXAMPLE 1

4.7 g of purified methylcarbamate and 6 g of LiTFSI were put into a round bottom flask and slowly stirred for 2 hours at a room temperature under a nitrogen circumstance, thereby obtaining 10.7 g of a eutectic mixture.

COMPARATIVE EXAMPLE 2

3.8 g of purified acetamide and 6 g of LiTFSI were put into a round bottom flask and slowly stirred for 2 hours under a nitrogen circumstance, thereby obtaining 9.8 g of a eutectic mixture.

COMPARATIVE EXAMPLE 3

5.3 g of oxazolidinone and 2 g of $LiPF_6$ were put into a round bottom flask and slowly stirred for 2 hours under a nitrogen circumstance, thereby obtaining 7.3 g of a eutectic mixture.

Evaluation of Properties of Electrolyte

In order to evaluate properties of the electrolytes prepared according to the above examples and the comparative examples, the following test was executed.

Evaluation of Viscosity and Ion Conductivity

With respect to the eutectic mixtures according to the examples 1 to 6 and the comparative examples 1 to 2, viscosity was measured using a RS150 viscometer at 25° C., and ion conductivity was measured using Inolab 740. The test results are shown in the following table 1.

TABLE 1

|  | Viscosity (cP) | Ion Conductivity (mS/cm) |
|---|---|---|
| Example 1 | 7.4 | 7.1 |
| Example 2 | 10.2 | 5.6 |
| Example 3 | 9.2 | 5.9 |
| Example 4 | 15.6 | 5.1 |
| Example 5 | 11.3 | 6.2 |
| Example 6 | 13.1 | 5.5 |
| Comparative Example 1 | 62.0 | 1.7 |
| Comparative Example 2 | 100.0 | 1.1 |

Seeing the table 1, it would be understood that the electrolyte of the present invention exhibits greatly improved viscosity and ion conductivity in comparison to electrolytes containing conventional eutectic mixtures.

Evaluation of Electrochemical Window

Electrochemical windows were measured using a Bistat Potentiostat for the eutectic mixtures according to the examples 1 to 3 in which an amide compound corresponding to the chemistry figure 1 is used as a component, and the eutectic mixtures according to the comparative examples 1 and 2. The measurement results are shown in the following table 2. Seeing the table 2, the eutectic mixtures according to the examples in which an amide compound containing an alkoxy alkyl group is used as a component exhibit lower reduction potential windows (lowest values of the potential windows) than the eutectic polymers of the comparative examples, so it would be understood that the reduction stability is improved.

TABLE 2

|  | Example 1 | Example 2 | Example 3 | Comparative example 1 | Comparative example 1 |
|---|---|---|---|---|---|
| Electrochemical Window (V) | 0.45~4.5 | 0.5~4.7 | 0.45~4.55 | 0.6~4.7 | 0.7~4.9 |

In addition, potential windows were measured for the eutectic mixture according to the example 4 in which an amide compound corresponding to the chemistry figure 2 is used as a component and the eutectic mixture according to the comparative example 3. The measurement results are shown in the following table 3. Seeing the table 3, it would be understood that the eutectic mixture according to the example 4 in which an amide compound containing an alkoxy alkyl group is used as a component exhibits improved reduction stability in comparison to the eutectic mixtures according to the comparative examples, so the reduction stability is improved.

TABLE 3

|  | Electrochemical Window |
|---|---|
| Example 4 | 0.8~4.7 |
| Comparative Example 3 | 1.1~4.8 |

Manufacture of Secondary Battery

EXAMPLE 7

Preparation of Cathode

LiCoO$_2$ as a cathode active material, artificial graphite as conductive material, and polyvinylidene fluoride as a binder were mixed at a weight ratio of 94:3:3, and then N-methylpyrrolidone was applied to the obtained mixture to make slurry. The prepared slurry was applied to an aluminum foil and then dried at 130° C. for 2 hours, thereby making a cathode.

Preparation of Anode

Anode active material, artificial graphite as conductive material, and a binder were mixed at a weight ratio of 94:3:3, and then N-methylpyrrolidone was applied to the obtained mixture to make slurry. The prepared slurry was applied to a copper foil and then dried at 130° C. for 2 hours, thereby making an anode.

Assembling of Secondary Battery

The made cathode and anode were prepared to have a size of 1 cm$^2$, and a separator was interposed between them. The electrolyte prepared in the example 1 was injected thereto, thereby making a secondary battery as shown in FIG. 1. In FIG. 1, reference numeral 1 designates a cathode, 2 designates an anode, 3 designates separator and electrolyte, 4 designates a spacer, 5 designates a coin can container, 6 designates a coil can cover, and 7 designates a seaming rubber.

EXAMPLE 8

2.3 g of the electrolyte prepared in the example 1 was injected to a commercial pouch-type battery in which a separator is interposed between a cathode and an anode configured as above, thereby making a secondary battery.

COMPARATIVE EXAMPLE 4

A secondary battery was made in the same way as the example 7, except that an electrolyte solution obtained by mixing 4.2 g of ethylene carbonate and 6.3 g of ethylmethyl carbonate and then dissolving 1.5 g of LiPF$_6$ thereto was used as electrolyte.

COMPARATIVE EXAMPLE 5

A secondary battery was made in the same way as the example 8, except that the electrolyte of the comparative example 1 was used instead of the electrolyte of the example 1.

Evaluation of Charging/Discharging Performance

The secondary batteries prepared according to the example 5 and the comparative example 4 were respectively charged/discharged by 0.5 mA, and discharge capacity and charging/discharging efficiency were measured according to cycles.

As a result of the experiment, it was found that both of the battery using the electrolyte containing a common carbonate-based solvent according to the comparative example 4 and the battery using the electrolyte of the present invention according to the example 7 exhibit 90% or more discharge capacity and 99% of charging/discharging efficiency after thirtieth cycles. In FIG. 2, a solid line represents the example 7, and a dotted line represents the comparative example 4. From FIG. 2, it might be understood that the electrolyte of the present invention may give performance equivalent to conventional commercialized liquid electrolytes.

Evaluation of Thermal Stability of Battery

In order to evaluate stability of a lithium secondary battery including the electrolyte according to the present invention, the following experiment was conducted.

Figure 3:
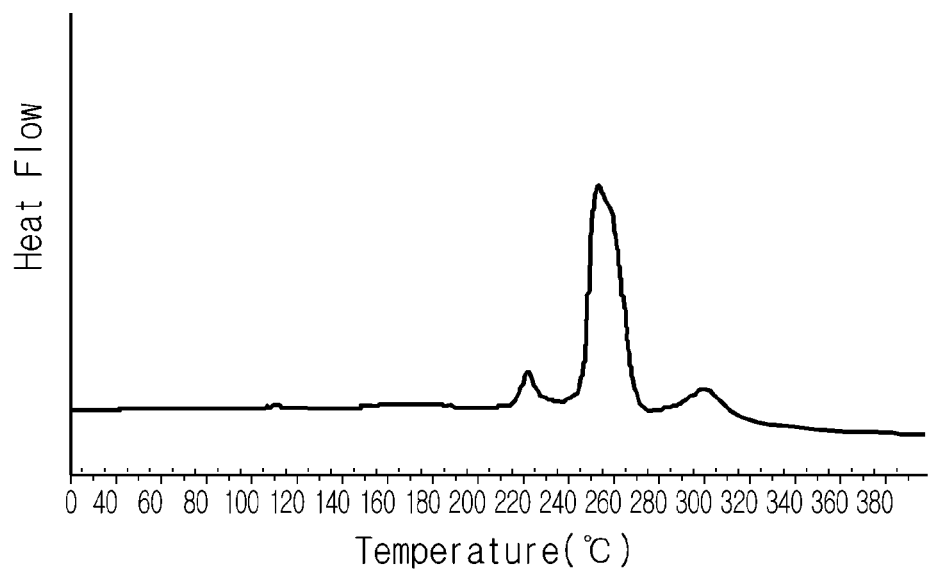
FIG. 3 is a graph showing DSC (Differential Scanning Calorimeter) analysis results of a charged $LiCoO_2$ electrode and an electrolyte, in the lithium secondary battery of the example 7.
Figure 4:
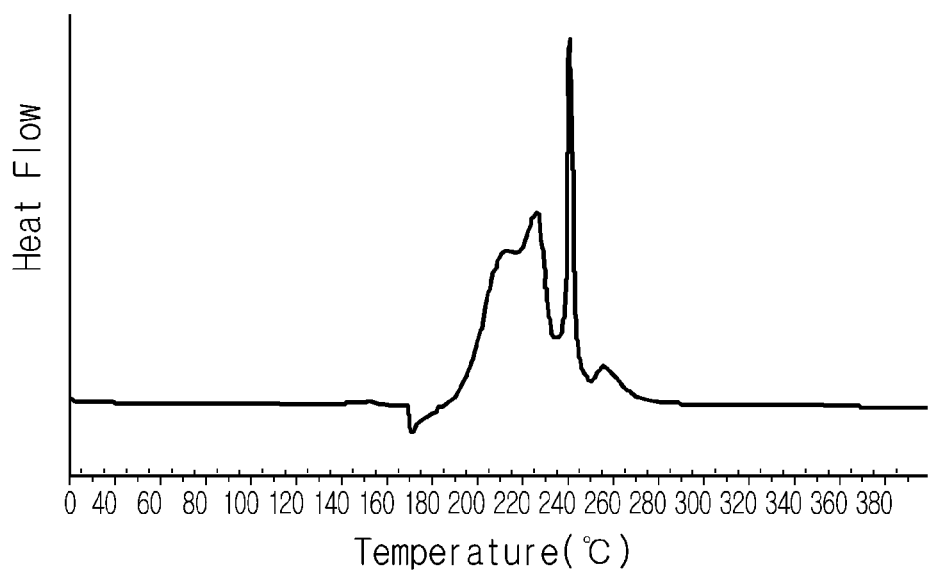
FIG. 4 is a graph showing DSC analysis results of a charged $LiCoO_2$ electrode and an electrolyte, in the lithium secondary battery of the comparative example 4.

The batteries prepared according to the example 7 and the comparative example 4 were charged at 23° C. to 4.2V, and then the batteries were dissembled to take out cathodes. For the taken cathodes, thermal stability against cathode and electrolyte was evaluated using DSC (Differential Scanning Calorimetry). FIGS. 3 and 4 are graphs showing DSC results for the batteries according to the example 7 and the comparative example 4, respectively. Their analysis results are shown in the following table 4.

TABLE 4

|  | Example 7 |  | Comparative Example 4 |  |
|---|---|---|---|---|
| Onset Temp (° C.) | 220 | 249 | 203 | 241 |
| Peak area (W/g) | 66 | 501 | 539 | 174 |

Referring to FIGS. 3 and 4, the battery of the example 7 shows that a greatest peak area with the greatest caloric value starts at 249° C., while the battery of the comparative example 4 having an electrolyte containing EC and EMC in mixture shows that a greatest peak starts at a lower temperature of 203° C. Thus, it could be found that the lithium secondary battery according to the example 7 of the present invention meaningfully controls side reactions between electrode active material and electrolyte, thereby, improving thermal stability of the battery.

High Temperature Stability Experiment of Secondary Battery

The pouch-type secondary batteries prepared according to the example 8 and the comparative example 5 were charged to 4.2V, and then left alone at 90° C. for 4 hours, and the change of thickness of the batteries were measured. The experimental results are shown in the following table 5.

TABLE 5

|  | Initial Thickness (mm) | Later Thickness (mm) | Increment (%) |
|---|---|---|---|
| Example 8 | 3.85 | 3.92 | 1.8% |
| Comparative Example 5 | 3.86 | 4.53 | 17.3% |

Seeing the table 5, it would be understood that the battery using the electrolyte of the present invention according to the example 8 exhibits more excellent high temperature stability than the battery using a conventional electrolyte according to the comparative example 5.

The invention claimed is:

1. An electrolyte, comprising:
   (a) an eutectic mixture of an alkoxy alkyl group-containing amide compound expressed by the following chemistry figure 1 or 2 and an ionizable lithium salt; and
   (b) a carbonate-based compound, Chemistry Figure 1

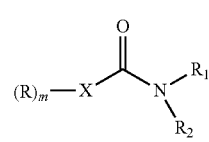

wherein R, $R_1$ and $R_2$ are hydrogen, halogen or any one selected from the group consisting of an alkyl group, alkylamine group, alkenyl group and aryl group having 1 to 20 carbons, independently, and at least one of $R_1$ and $R_2$ is an alkoxy alkyl group expressed by $CH_3$—$(CH_2)$p-$O(CH_2)q$, wherein p is an integer of 0 to 8 and q is an integer of 1 to 8, and X is any one selected from the group consisting of silicon, oxygen, nitrogen, phosphorus, sulfur and hydrogen, and i) m is 0 (zero) when X is hydrogen, ii) m is 1 when X is oxygen or sulfur, iii) m is 2 when X is nitrogen or phosphorus, and iv) m is 3 when X is silicon;

Chemistry Figure 2

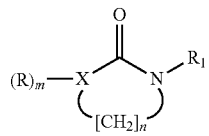

wherein R is hydrogen, or any one selected from the group consisting of an alkyl group, alkylamine group, alkenyl group, aryl group and allyl group having 1 to 20 carbons, and $R_1$ is an alkoxy alkyl group expressed by $CH_3$—$(CH_2)p$-$O(CH_2)q$, wherein p is an integer of 0 to 8 and q is an integer of 1 to 8, X is any one selected from the group consisting of silicon, oxygen, nitrogen, phosphorus and sulfur, and i) m is 0 (zero) when X is oxygen or sulfur, ii) m is 1 when X is nitrogen or phosphorus, and iii) m is 2 when X is silicon, and n is an integer of 1 to 10; and wherein the eutectic mixture comprises the alkoxy alkyl group-containing amide compound and the lithium salt at a mole ratio of 1-8: 1.

2. The electrolyte according to claim 1, wherein the alkoxy alkyl group-containing amide compound is any one selected from the group consisting of N-methoxyethyl methylcarbamate, N-methoxyethyl-N-methyl methylcarbamate, N-methoxymethyl-N-methyl methylcarbamate, N-methyl-methoxymethyl methoxyethyl carbamate, N-methyl-N-methoxyethyl methoxyethyl carbamate, N-methyl-N-methoxyethyl methoxymethyl carbamate, N-methoxyethyl caprolactam, N-methoxyethyl oxazolidinone, N-methoxyethyl-N-methyl phenyl thiocarbamate, and N-methoxyethyl-N-methyl piperidine carbamate.

3. The electrolyte according to claim 1, wherein an anion of the lithium salt is any one selected from the group consisting of $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$ and $(CF_3CF_2SO_2)_2N^-$.

4. The electrolyte according to claim 1, wherein the eutectic mixture comprising the alkoxy alkyl group-containing amide compound expressed by the chemistry figure 1 and the ionizable lithium salt has a reduction potential window of 0.4 to 0.55V, and the eutectic mixture comprising the alkoxy alkyl group-containing amide compound expressed by the chemistry figure 2 and the ionizable lithium salt has a reduction potential window of 0.7 to 0.9V.

5. The electrolyte according to claim 1, wherein the carbonate-based compound is any one selected from the group consisting of linear carbonate, cyclic carbonate, and their mixtures.

6. The electrolyte according to claim 5, wherein the carbonate-based compound is any one selected from the group consisting of propylene carbonate (PC), ethylene carbonate (EC), diethyl carbonate (DEC), dimethyl carbonate (DMC), dipropyl carbonate (DPC), butylene carbonate, methylpropyl carbonate, ethylpropyl carbonate, dimethyl sulfoxide, acetonitrile, dimethoxyethane, diethoxyethane, tetrahydrofuran, N-methyl-2-pyrrolidone (NMP), ethylmethyl carbonate (EMC), γ-butyrolactone), and their mixtures.

7. The electrolyte according to claim 1, wherein the content of the carbonate-based compound is 5 to 200 parts by weight, based on 100 parts by weight of the eutectic mixture.

8. The electrolyte according to claim 1, wherein the electrolyte has a viscosity of 50 cP or less.

9. The electrolyte according to claim 8, wherein the electrolyte has a viscosity of 4 to 30 cP.

10. The electrolyte according to claim 1, wherein the electrolyte has an ion conductivity of 5 to 10 mS/cm.

11. The electrolyte according to claim 1, wherein the electrolyte is a polymer electrolyte.

12. The electrolyte according to claim 11, wherein the polymer electrolyte is a gel-type polymer electrolyte formed by polymerizing a precursor solution containing: (i) a mixture of the eutectic compound in the above (a) and the carbonate-based compound in the above (b); and (ii) a monomer, at the same time.

13. The electrolyte according to claim 12, wherein the monomer is a vinyl monomer.

14. The electrolyte according to claim 13, wherein the vinyl monomer is any one selected from the group consisting of acrylonitrile, methylmethacrylate, methylacrylate, methacrylonitrile, methylstyrene, vinylester, vinyl chloride, vinylidene chloride, acrylamide, tetrafluoroethylene, vinylacetate, methylvinylketone, ethylene, styrene, paramethoxystyrene, paracyanostyrene, and their mixtures.

15. The electrolyte according to claim 12, wherein the gel-type polymer electrolyte is obtained by in-situ polymerization in an electrochemical device.

16. The electrolyte according to claim 11, wherein the polymer electrolyte is obtained by impregnating in a polymer the mixture of the eutectic mixture in the above (a) and the carbonate-based compound in the above (b).

17. The electrolyte according to claim 16, wherein the polymer is any one selected from the group consisting of polymethylmethacrylate, polyvinylidene difluoride, polyvinyl chloride, polyethylene oxide, polyhydroxyethylmethacrylate, and their mixtures.

18. An electrochemical device, comprising a cathode, an anode and an electrolyte, wherein the electrolyte is an electrolyte defined in claim 1.

19. The electrochemical device according to claim 18, wherein the electrochemical device is a lithium secondary battery.

20. The electrochemical device according to claim 19, wherein the lithium secondary battery is a pouch-type secondary battery, and the pouch-type secondary battery has a thickness change ratio of 10% or less after being charged to 4.2V and then left alone at 90° C. for 4 hours.

* * * * *